(12) United States Patent
Behiels

(10) Patent No.: US 9,031,193 B2
(45) Date of Patent: May 12, 2015

(54) METHOD OF GENERATING A RADIATION IMAGE OF AN ELONGATE BODY

(75) Inventor: Gert Behiels, Edegem (BE)

(73) Assignee: Agfa HealthCare NV, Mortsel (BE)

( * ) Notice: Subject to any disclaimer, the term of this patent is extended or adjusted under 35 U.S.C. 154(b) by 123 days.

(21) Appl. No.: 14/008,134

(22) PCT Filed: Mar. 28, 2012

(86) PCT No.: PCT/EP2012/055448
§ 371 (c)(1),
(2), (4) Date: Sep. 27, 2013

(87) PCT Pub. No.: WO2012/136520
PCT Pub. Date: Oct. 11, 2012

(65) Prior Publication Data
US 2014/0016755 A1  Jan. 16, 2014

Related U.S. Application Data

(60) Provisional application No. 61/472,766, filed on Apr. 7, 2011.

(30) Foreign Application Priority Data

Apr. 7, 2011 (EP) .................................... 11161506

(51) Int. Cl.
*A61B 6/00* (2006.01)
*A61B 6/04* (2006.01)

(52) U.S. Cl.
CPC ................ *A61B 6/5241* (2013.01); *A61B 6/04* (2013.01); *A61B 6/50* (2013.01); *A61B 6/5217* (2013.01); *A61B 6/5235* (2013.01)

(58) Field of Classification Search
CPC ..................................................... A61B 6/5241
See application file for complete search history.

(56) References Cited

U.S. PATENT DOCUMENTS

| | | | |
|---|---|---|---|
| 6,895,076 B2* | 5/2005 | Halsmer et al. | 378/98.12 |
| 7,110,497 B2* | 9/2006 | Halsmer et al. | 378/98.12 |
| 7,555,100 B2* | 6/2009 | Wang et al. | 378/98.12 |
| 2008/0152088 A1 | 6/2008 | Wang et al. | |
| 2009/0245464 A1 | 10/2009 | Yamaguchi | |
| 2014/0072198 A1* | 3/2014 | Moon et al. | 382/131 |

FOREIGN PATENT DOCUMENTS

| | | |
|---|---|---|
| EP | 1 484 016 A1 | 12/2004 |
| EP | 2 497 424 A1 | 9/2012 |
| WO | 2007017790 A2 | 2/2007 |

OTHER PUBLICATIONS

International Search Report, mailed May 29, 2012, from counterpart International Application No. PCT/EP2012/055448, filed Mar. 28, 2012.

* cited by examiner

*Primary Examiner* — Jack Berman
(74) *Attorney, Agent, or Firm* — Keating & Bennett, LLP

(57) ABSTRACT

Method of generating a radiation image of an elongate body by taking plural partial X-ray images on a digital radiography detector using a multiple shot exposure technique. Partial image dimensions are determined so that the partial image representing that part of the elongate body that is most susceptible of movement during the multiple shot exposure is recorded covering an as large as possible area of the detector.

5 Claims, 8 Drawing Sheets

Figure 5 UArm.svg

METHOD OF GENERATING A RADIATION IMAGE OF AN ELONGATE BODY

RELATED APPLICATIONS

This application is a §371 National Phase Application of International Application No. PCT/EP2012/055448, filed on Mar. 28, 2012, now International Publication No. WO 2012/136520 A1, published on Oct. 11, 2012, which International Application claims the benefit under 35 U.S.C. §119(e) of U.S. Provisional Application No. 61/472,766, filed on Apr. 7, 2011, and also claims priority to European Application No. EP 11161506.8, filed on Apr. 7, 2011, all three of which are incorporated herein by reference in their entirety.

FIELD OF THE INVENTION

The present invention relates to a method of generating a radiation image of an elongate body by taking plural partial X-ray images on a digital radiography detector using a multiple shot exposure technique.

BACKGROUND OF THE INVENTION

In radiography, sometimes an image of a region with long length is taken, such as the entire spine or the legs. In Computed Radiography (CR), images are taken with Imaging Plates (IP) which partially overlap each other and a long length image is created by combining the partial images. Accurate alignment and measurement can be obtained by superimposing an object of known geometry covering the region to be imaged and correcting and aligning the partial images to reconstruct the object of known geometry (see EP0919858, EP0866342). This technique does not suffer from patient movement since all images are acquired in a single X-ray exposure.

In recent years, Digital Radiography (DR) has become a valuable alternative for CR. The flat panel detectors (FPD) used in DR are more costly than the IPs for CR, so an alternative to the one-shot long length imaging technique of CR is needed. This is achieved by taking plural partial images by moving the position of the FPD while turning the X-ray tube or moving the X-ray tube parallel to the FPD and pasting the partial images to obtain a composed long length image. During this FDP and X-ray tube movement, the patient may move, hereby introducing artifacts which need to be compensated in the image composition.

Long length images are mostly taken to perform length and angle measurements on the subject across an area larger than a single FPD.

It is therefore important to create an image where the alignment of the partial images of the subject and the calibration is accurate. If the patient is capable to stand still perfectly, this can be accomplished with known techniques such as described in the co-pending European application EP11157111.3 filed on Mar. 7, 2011 entitled 'Radiographic imaging method and apparatus'. Unfortunately, most patients requiring a long length examination suffer from a condition which makes it difficult to stand still during the time of the image acquisition. Therefore, the partial images are positioned with a certain amount of overlap such that a user is capable of positioning the partial images to form a composite image based on the image content in the area of the overlap.

In order to reduce the amount of X-ray exposure, images with different sizes are needed. This can be accomplished by manipulation of the collimator which is adjusted to block the x-rays based on the size of the exposure, hereby reducing exposure to the subject.

European patent application 1 484 016 A1 relates to the acquisition of a composite image with a digital detector. Positions of individual component images of the composite image are calculated. First the structures that tend to move are identified and then non-uniform collimation angles may be used for the different component images to avoid placing these structures in the regions of overlap. This method requires identification or estimation of the position of these structures.

It is an object of the present invention to optimize the calculation of the sizes of the partial images so as to reduce the above-mentioned problems occurring in imaging elongate bodies and originating from patient movement during multiple shot exposure and image recording.

SUMMARY OF THE INVENTION

The above-mentioned aspects are realised by a method having the specific features set out in claim 1. Specific features for preferred embodiments of the invention are set out in the dependent claims.

The method of the present invention comprises the steps of generating a sequence of partially overlapping partial radiation images of said elongate body by multiple shot irradiation and read out of a direct radiography detector and pasting the partial images to form a composite image.

According to the present invention the size and position of the partial images is determined on the basis of the calculated number of partial images so that the partial image representing a part of the elongate body which is most susceptible to movement during said multiple shot irradiation covers a larger area than the area covered by partial images representing parts of the elongate body less susceptible to movement.

Preferably the length of the partial image which is most susceptible of movement during the multi-shot exposure covers substantially the entire radiation sensitive area of the detector if this configuration is allowed by the physical constraints of the imaging system which is used.

In a preferred embodiment, the length of the partial images is calculated so that the part of the patient that is most susceptible to movement during the multiple-shot exposure is recorded in one shot on a single detector area. The width of the partial images is commonly constant. The setting of the partial image's length is achieved by appropriate setting of the x-ray source and radiation shutter or collimator.

For images of an elongate body such as full spine or full leg images where the patient is standing in upright position, it has been observed that the amount of movement is larger for positions higher from the ground. There are two main reasons for this observation. First, movement is introduced by the patient's breathing which is inherently positioned at a high position. Secondly, a patient is more stable and steady at positions near the ground. This is illustrated in FIG. 1. With this observation, it has been decided that it is best to take the highest images as large as possible (given the detector's dimensions) to minimize the corrections needed to compensate the patient movement.

When a full spine image is taken of a patient in a horizontal position, the body part that is most susceptible of movement may be the upper body part. However in case of a lying patient for whom a full leg image is taken, this may be the lower part of the legs.

In up-right position, physical constraints may imply that the lower image is an image which covers the largest part of the detector. In that case the lengths of the other partial images are calculated so that the partial image corresponding with the body part that is most susceptible to movement during the multi-shot exposure covers substantially the entire radiation sensitive part of the radiation detector.

According to an embodiment of the present invention the total length of the elongate body to be imaged is first determined.

Next, on the basis of the determined length and (a) predefined amount(s) of overlap between said partial images, the number of partial images required to image the elongate body is calculated.

Then, on the basis of the calculated number of partial images, the size and position of the partial images is calculated so that the partial image which comprises the body part that is most susceptible of movement during the multi-shot exposure is imaged on a larger area (preferably substantially the entire area) of the x-ray sensitive detector area than the area covered by the other partial images. The size and position of partial images may be expressed by settings of x-ray source and collimator or x-ray shutter.

The size (length) of a partial image can be input by the user or can be calculated by a processor. Alternatively it can be input by a device capable of indicating the size on the patient.

The partial images generated by multiple shot exposure are read out and pasted to form an elongate image.

Further advantages and embodiments of the present invention will become apparent from the following description and drawings.

DETAILED DESCRIPTION OF THE INVENTION

X-ray systems capable of performing long length imaging are available in different configurations, each controlled differently to obtain optimal results for long length imaging. Common parts of the configurations are: an X-ray generation unit including an X-ray source that generates x-rays; a collimator unit which is adjustable and reduces the area on which X-rays are projected; an X-ray imaging unit capable of collecting images based on the generated X-rays.

Most modern systems include controllers to control the X-ray generation unit and X-ray imaging unit. Automatic systems, needed to perform automatic long length imaging, also include position mechanisms and controllers for the positions of the X-ray generation and X-ray imaging unit. In systems such as a C-Arm or U-Arm, some mechanisms and controllers are combined.

According to the present invention it has been decided to take the partial image representing that part of the elongate body which is most susceptible of movement during the multiple shot exposure as large as possible (given the detector dimensions) to minimize the corrections needed to compensate for the occasional patient movement. This has the added advantage that for a regular up-right full spine image starting from the atlas, for most patients the area containing the lungs and the heart is imaged in a single shot. This further reduces the artifacts introduced by the patient movement and avoids double exposure of the heart.

Most prior art systems divide the area which needs imaging into equal parts. This reduces the complexity and the number of computations involved to position the X-ray generation and X-ray imaging unit correctly.

In the next sections, formulas for a ceiling suspended system and a U-Arm will be derived to take the largest images at the highest positions when the patient is in an up-right position.

It will be clear that similar formulae may be derived for calculating partial image dimensions (expressed by means of settings for x-ray source, collimator and detector) when the body part that is most susceptible of movement is in another position and the dimensions of that partial image is as large as possible given the detector's dimensions.

Ceiling Suspended or Floor Mounted System

Figure 1:
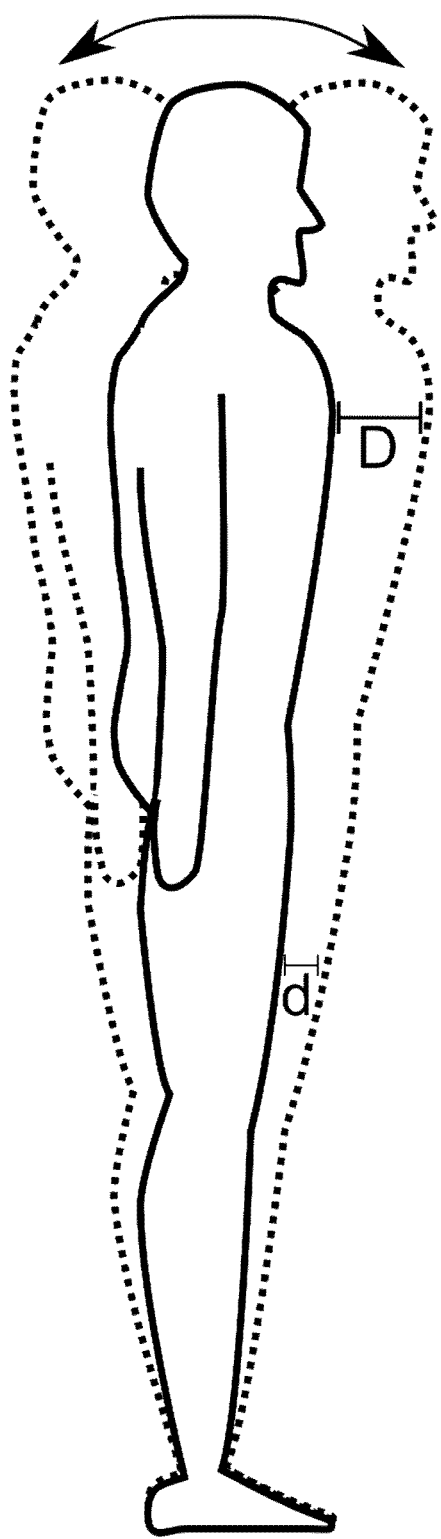
FIG. 1 is an illustration of the fact that a patient un up-right position is more stable closer to the ground. The displacement at the height of the legs (d) is much smaller than the displacement at the chest (D)
Figure 2:
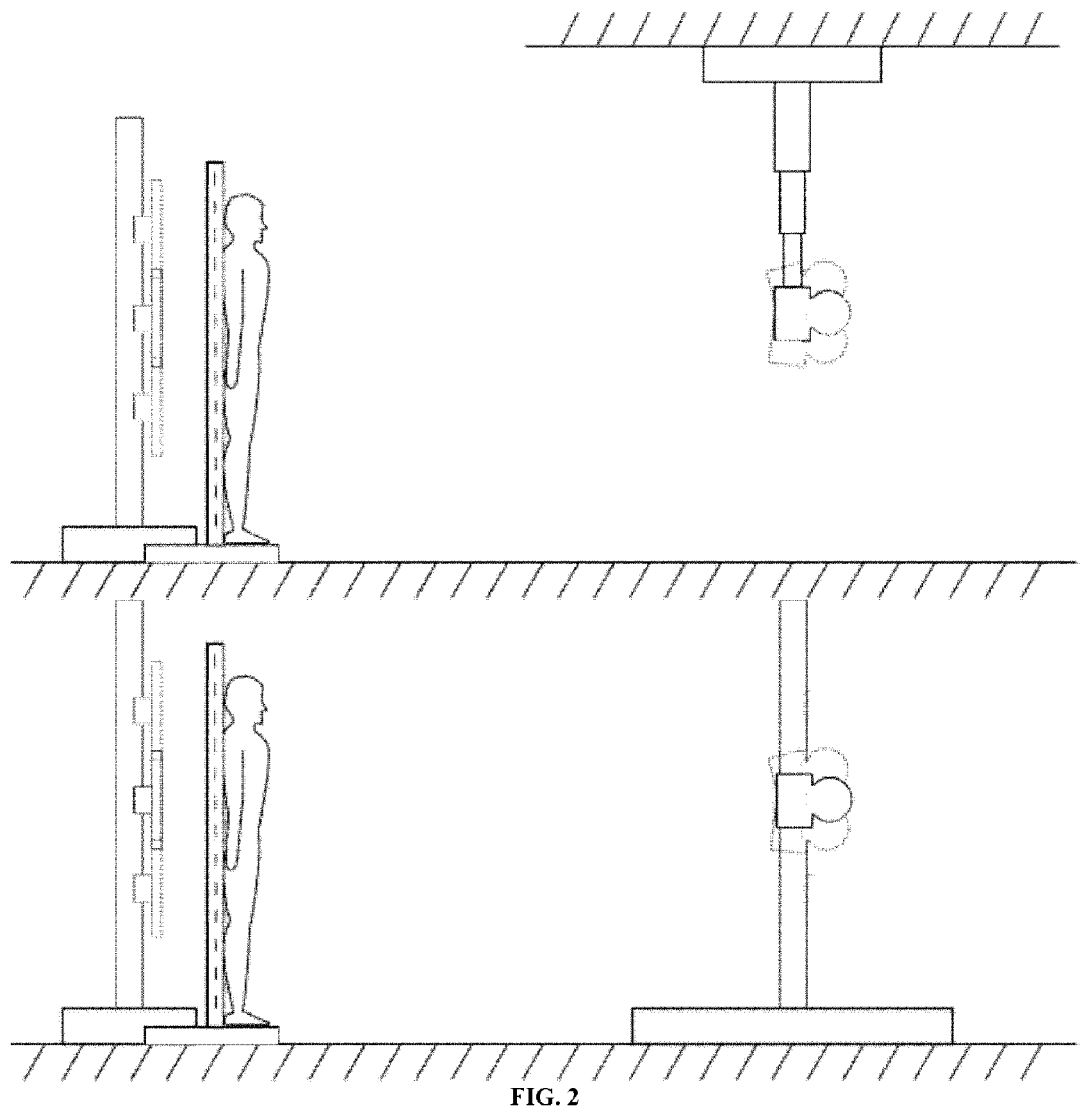
FIG. 2 is an illustration of a ceiling suspended and a floor mounted system supporting tube rotation.

For a ceiling suspended (or floor mounted) system where the X-ray source can rotate independently from the X-ray imaging unit, depicted in FIG. 2, the computations involved are given below.

Given a top position T and a bottom position B, the total length L for imaging is obtained by $$L=T-B.$$

Figure 3:
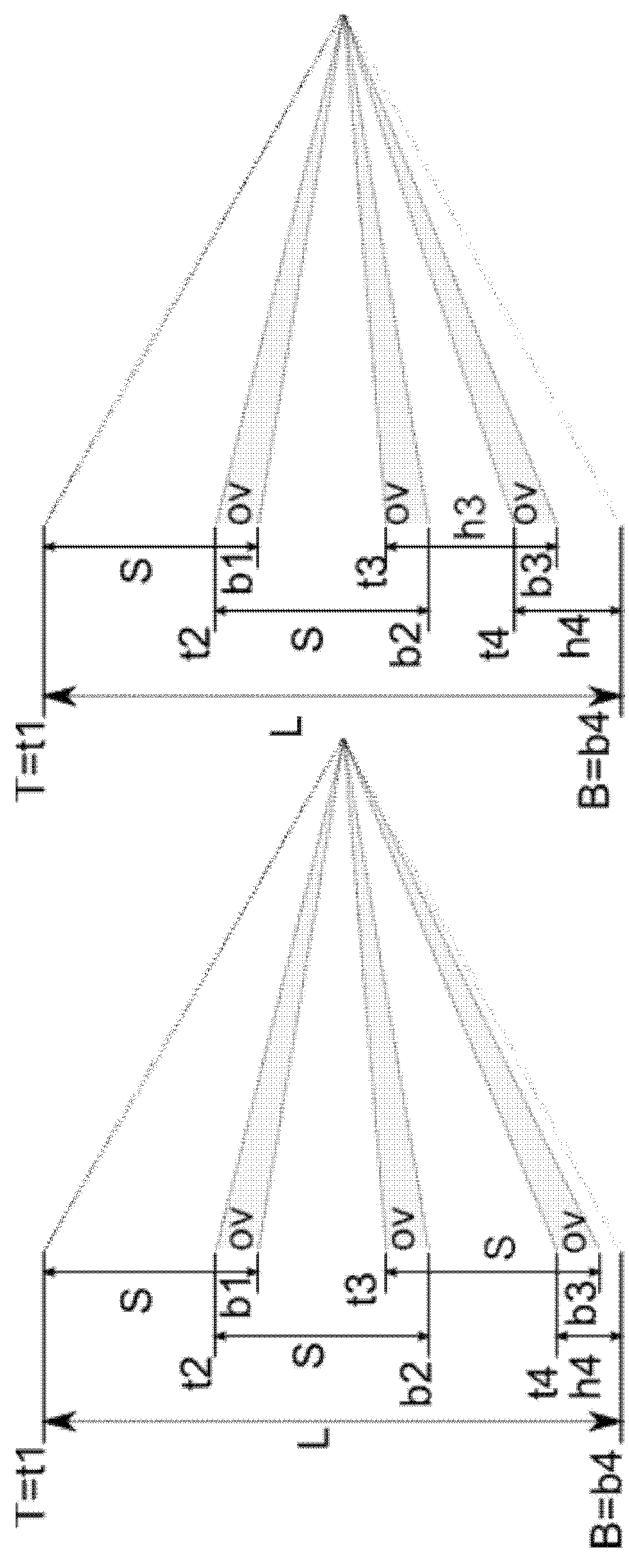
FIG. 3 is an illustration of the positions of the four partial images for a given input area with length L. The left figure uses the complete detector for the highest three images. The right figure is an illustration of a setup where only the 2 highest images use the complete detector.
Figure 4:
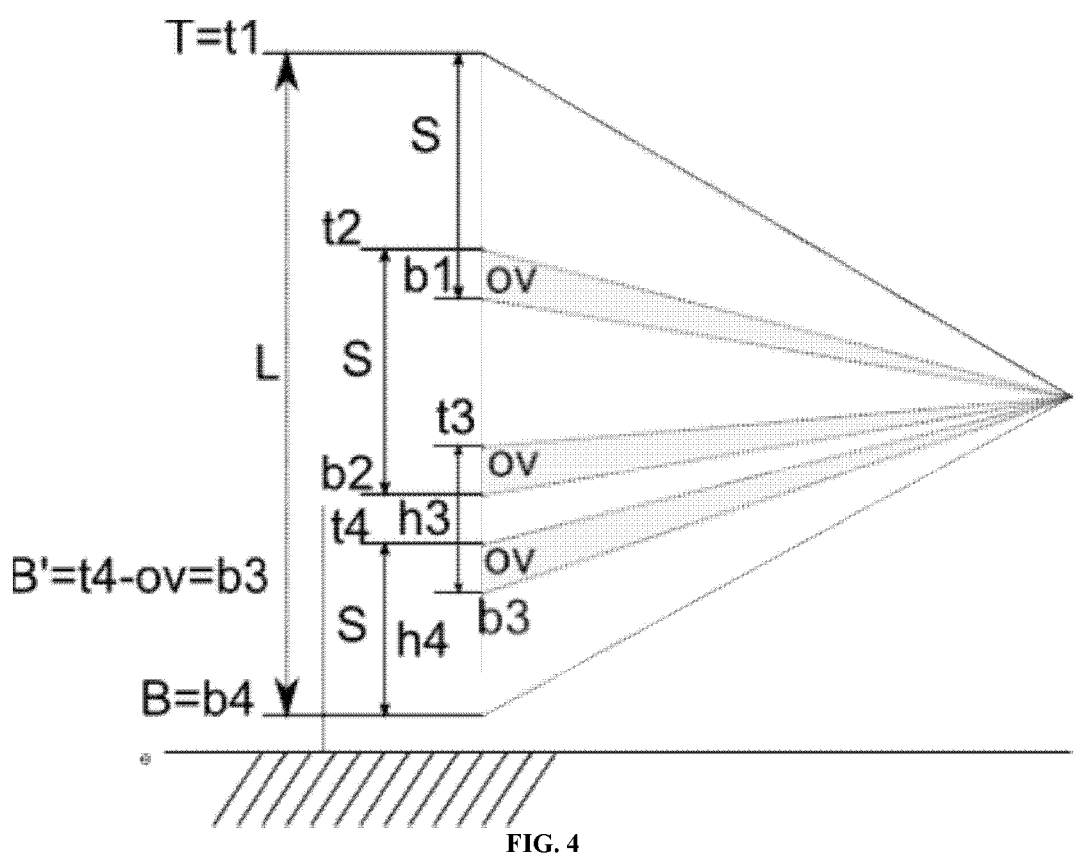
FIG. 4 is an illustration of a setup where the bottom image needs to be bigger than the second lowest image because otherwise the detector will collide with the floor.

Illustrations which clarify the variables and geometry are given in FIG. 3 and FIG. 4. The number of partial images N in which this area needs to be divided is $$N = smallest\ integer \geq \left(\frac{L-ov}{S-ov}\right),$$

where S is the maximum height the detector can image and ov is the desired amount of overlap.

This allows us to calculate the top positions $t_i$ and bottom positions $b_i$ for each partial image where $$t_1 = T$$

$$b_i = t_i + S, \forall i : i \leq N-1$$

$$t_{i+1} = b_i - ov, \forall i : 1 < i \leq N$$

$$b_N = B$$

From each pair of positions $t_i$, $b_i$, the position of the center height and collimator size for each partial image is easily computed with following equations:

$$y_i = \frac{t_i - b_i}{2},$$

$$h_i = t_i - b_i.$$

Most modalities support the combination of the values $(y_i, h_i)$ as part of the input to position the detector and adjust the collimator.

When looking at the left part of FIG. 3, we see that such a computation scheme can lead to very small partial images at the bottom of the area. This can easily be prevented by changing the computation scheme if a condition such as e.g.

$$t_N - b_N - ov < \frac{t_{N-1} - b_{N-1} - ov}{2}, N \geq 2,$$

is true. A new scheme which can be used in such conditions is $$s = \begin{cases} b_{N-2}, N > 2 \\ T, N = 2 \end{cases}$$

$$R = s - B$$

$$t_{N-1} = \begin{cases} s - ov, N > 2 \\ s, N == 2 \end{cases}$$

$$b_{N-1} = s + \frac{2}{3}R + ov.$$

FIG. 3 illustrates the differences between the new computation scheme (right side) and the old computation scheme (left side).

Because long length imaging is often used to acquire images from the legs, the computation schemes described above can position the imaging unit to a location which is unreachable. This is illustrated in FIG. 4. Because the imaging unit has fixed dimensions, the previously proposed computation scheme can not be used because the imaging unit would be positioned below the ground. Suppose e is the lowest point which can be imaged by the detector at its lowest position, we can redefine a variable B' for which we apply the computation schemes above but now with B' as bottom position and a resulting number of N'+1 positions:

$$N' = smallest\, integer \geq \left( \frac{T - B' - ov}{S - ov} \right)$$

$$t'_{N'+1} = 2e + S - B$$

$$b'_{N'+1} = B$$

$$B' = t'_{N'+1} - ov$$

U-Arm Configuration

Figure 5:
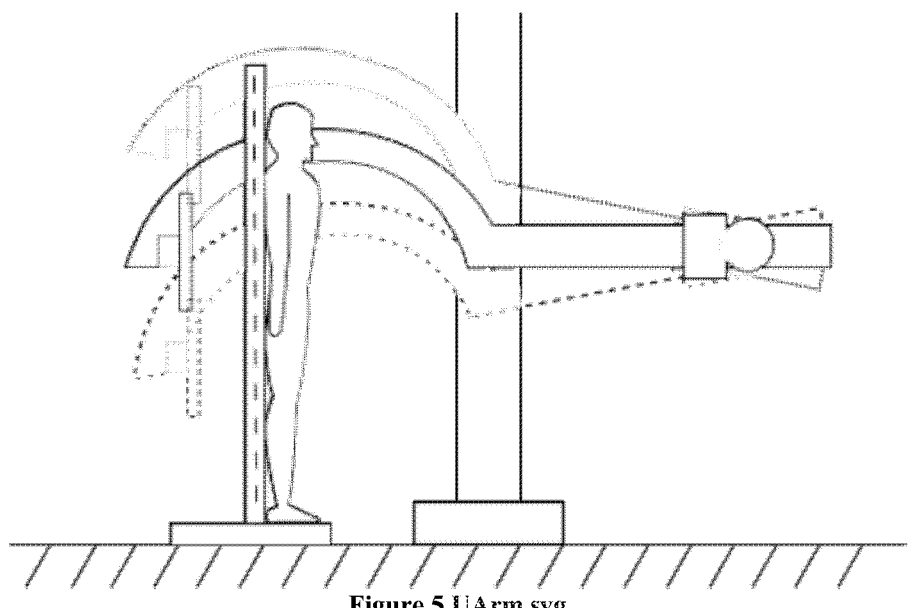
FIG. 5 is an illustration of a U-Arm which is positioned in such a way to keep the X-ray source stable for three positions.
Figure 6:
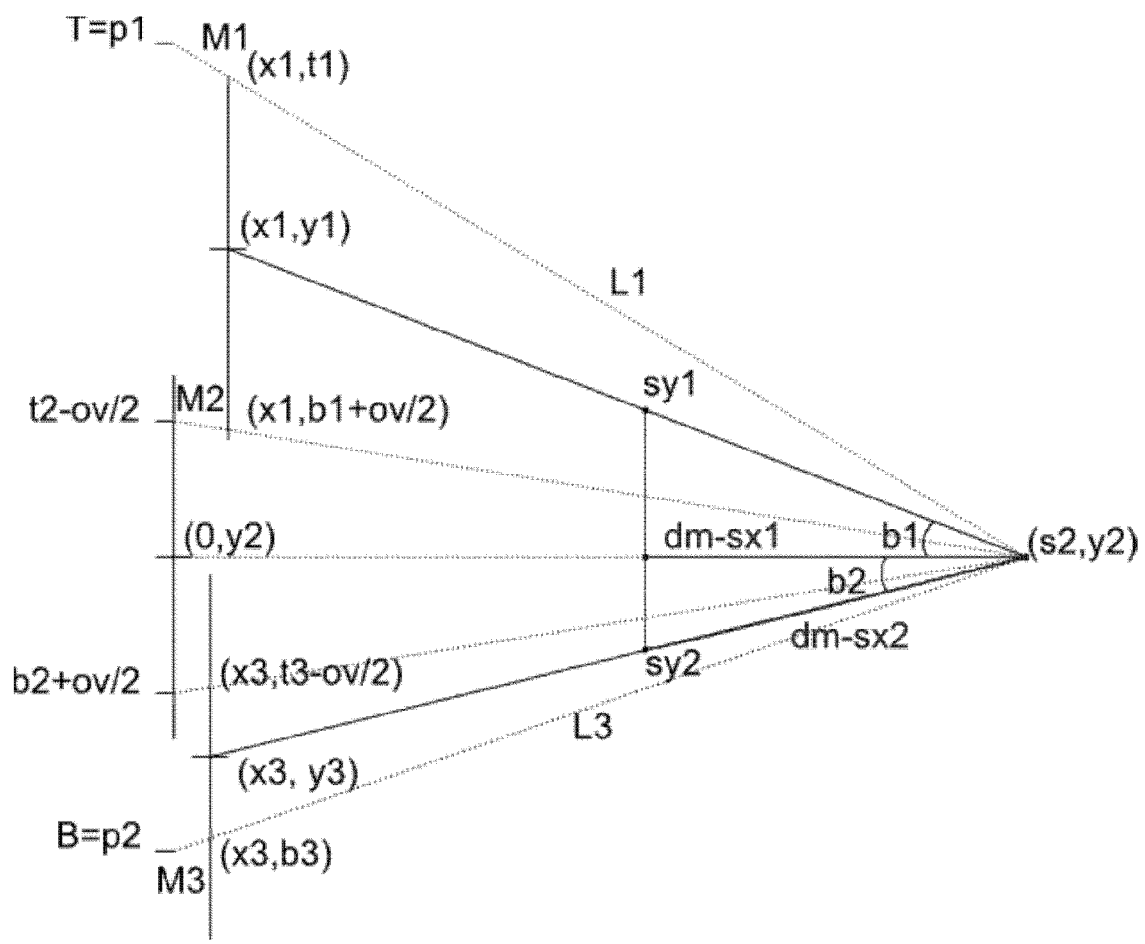
FIG. 6 is the description of the geometry and its variables used in the calculations to compute the positions of a U-Arm in a three image setup.

The computations involved to correctly position the detector part of a U-Arm while keeping the X-ray source stable are given below. An illustration of a typical U-Arm configuration is given in FIG. 5. A schematic representation of an U-Arm for a sequence with 3 partial images is given in FIG. 6, in which the line [sy1-sy2] represents the positions where the point of rotation of the U-arm can only move in the vertical way. If we use the complete detector for the first partial image $$t_1 - b_1 = S,$$

and put the source of the X-rays at position $y_2 = 0$, we can describe the geometry with following equations:

$$d_f + d_m \cos\beta_1 = s_2$$

$$d_m \sin\beta_1 = s_{y1}$$

$$\frac{T}{t_1} = \frac{d_f + d_m \cos\beta_1}{(d_f + d_m)\cos\beta_1}$$

$$t_1 - \frac{S}{2} = (d_f + d_m)\sin\beta_1$$

$$d_f = x_1 + d_f \cos\beta_1$$

where $d_f$ is the distance between the detector and point of rotation of the U-Arm and $d_m$ is the distance from the point of rotation of the U-Arm to the X-ray source for the top partial image. Solving these equations for T gives $$T = \frac{\sec\beta_1(d_f + d_m\cos\beta_1)(S + 2\sin\beta_1(d_f + d_m))}{2(d_f + d_m)}.$$

Similar to the derivation above, we can deduce the position of $t_2$ in function of $d_f, d_m, \beta_1$ by solving $$d_f + d_m\cos\beta_1 = s_2$$

$$d_m\sin\beta_1 = s_{y1}$$

$$b_1 + \frac{S}{2} = (d_f + d_m)\sin\beta_1$$

$$d_f = x_1 + d_f\cos\beta_1$$

$$\frac{t_2 - \frac{ov}{2}}{s_2} = \frac{b_1 + \frac{ov}{2}}{(d_f + d_m)\cos\beta_1}$$

for $t_2$:

$$t_2 = \frac{d_m(2ov - S + 2d_m\sin\beta_1) + 2d_f^2\tan\beta_1 + d_f(ov + (ov - S)\sec\beta_1 + 2d_m(\sin\beta_1 + \tan\beta_1))}{2(d_f + d_m)}$$

Similar to the derivation of a computation scheme for the ceiling suspended system, we can describe 2 situations. In the first situation, we assume the second partial image is taken using a complete detector. In the second situation, the area between $(t_2-ov/2, b_2+ov/2)$ will be twice as large as the area between $(b_2+ov/2, B)$.

The first situation can be explored as follows:

$$t_2 = \frac{S}{2}.$$

Figure 7:
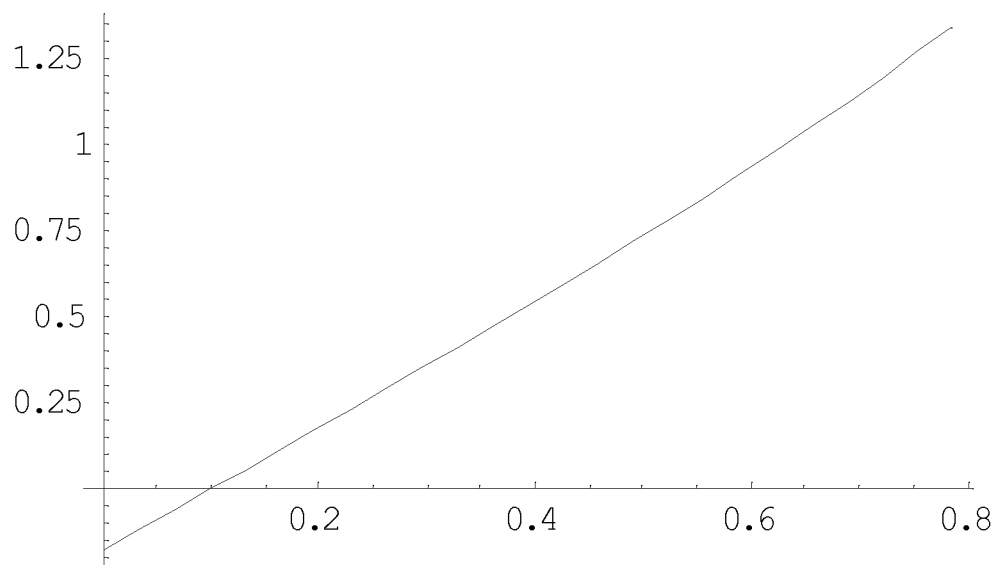
FIG. 7 illustrates the function of $y_3$ in function of $\beta_1$ with given $d_f=1, d_m=0.8, S=0.43, ov=0.07$.

Solving both equations for $t_2$ in $\beta_1$ when $ov, S, d_m, d_f$ is given, is possible but computational extensive. Since the equation for $t_2$ in $\beta_1$ behaves nice for optimization (see FIG. 7), it is also possible to determine the value for $\beta_1$ numerically.

In the second situation, the value for $t_2$ should be (again under the assumption that our X-ray source is positioned at $y_2=0$ and B is a negative value)

$$t_2 = \frac{ov - B}{2}.$$

Again both an analytical solution as a numerical solution are possible for $\beta_1$, where the numerical is preferred because of the lengthy computations involved in the analytical solution.

The formulas above generate all the necessary information for the positions of the first 2 images, to find the position of the last partial image we first determine the position of $y_3$ in function of $\beta_1, \beta_2$:

$$y_3 = s_3 \sin \beta_2$$

$$s_3 = d_f + d_m - s_{x2}$$

$$s_2 = d_f + d_m - s_{x1}$$

$$d_m - s_{x1} = (d_m - s_{x2})\cos \beta_2$$

$$s_2 = d_f + d_m \cos \beta_1$$

This leads to $$y_3 = \tan \beta_2 (d_f \cos \beta_2 + d_m \cos \beta_1). \qquad \text{Equation 1}$$

To find another function of $y_3$ in function of $\beta_1$, $\beta_2$, first determine functions for $t_3$ and $b_3$. Given $$s_2 - x_3 = s_3 \cos\beta_2$$
$$s_3 = d_f + d_m - s_{x2}$$
$$s_2 = d_f + d_m - s_{x1}$$
$$s_2 = d_f + d_m \cos\beta_1$$
$$d_m - s_{x1} = (d_m - s_{x2})\cos\beta_2$$
$$\frac{s_2 - x_3}{t_3} = \frac{s_2}{t_2 - \frac{ov}{2}}$$

we find $$t_3 = \frac{(d_f \cos\beta_2 + d_m \cos\beta_1)(t_2 - ov/2)}{d_f + d_m \cos\beta_1}.$$

Given $$s_2 - x_3 = s_3 \cos\beta_2$$
$$s_3 = d_f + d_m - s_{x2}$$
$$s_2 = d_f + d_m - s_{x1}$$
$$s_2 = d_f + d_m \cos\beta_1$$
$$d_m - s_{x1} = (d_m - s_{x2})\cos\beta_2$$
$$\frac{B}{s_2} = \frac{b_3}{s_2 - x_3}$$

the solution for $b_3$ is $$b_3 = \frac{B(d_f \cos\beta_2 + d_m \cos\beta_1)}{d_f + d_m \cos\beta_1}.$$

If we substitute the functions for $t_3$ and $b_3$ in $$2(t_3 - y_3) = t_3 - b_3 + \frac{ov}{2}$$

we get $$y_3 = \frac{2d_m \cos\beta_1 (B - ov + t_2) + d_f(-ov + \cos\beta_2(2B - ov + 2t_2))}{4(d_f + d_m \cos\beta_1)} \qquad \text{Equation 2}$$

Again, an analytical solution for $\beta_2$ exists but requires a lot of computational effort. Numerical solutions for the quadratic difference between Equation 1 and Equation 2 with all parameters fixed except $\beta_2$, will converge rapidly to the solution of $\beta_2$. It is clear that similar computations can be used for a setup with 2 or more images or for situations where the detector is positioned near the ground.

Figure 8:
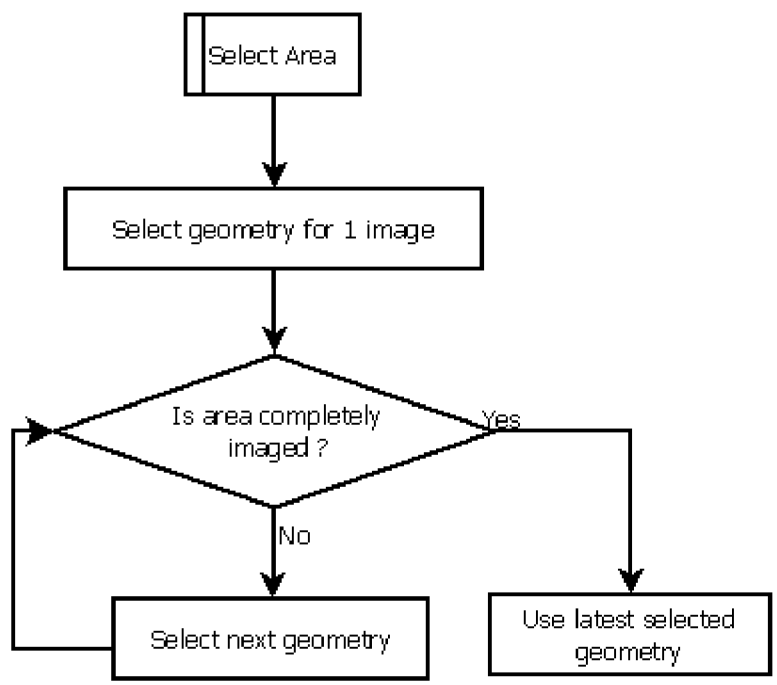
FIG. 8 is a flowchart describing the steps involved to select the number of images and geometry configuration for a system capable of performing long length imaging.

In order to determine the number of partial images needed to cover a given area, no single formula exists. A solution is to use an algorithm which selects the suitable geometry. Such an algorithm is depicted in FIG. 8.

An example order of geometries for a U-Arm is:
Geometry for 1 partial image
Geometry for 2 partial images: top partial image covers ⅔ of area, bottom partial images covers ⅓
Geometry for 2 partial images: top partial image uses complete detector
Geometry for 3 partial images: top partial image uses complete detector, middle partial image covers ⅔ of area minus top image, bottom partial image covers ⅓
Geometry for 3 partial images: top and middle partial images use complete detector.

The invention claimed is:

1. Method of generating a radiation image of an elongate body by generating a sequence of partially overlapping partial radiation images of said elongate body by multiple shot irradiation and read out of a direct radiography detector, comprising:
    determining the total length of said elongate body to be imaged;
    calculating on the basis of said determined length and (a) predefined amount(s) of overlap between said partial images, the number of partial images required to image said elongate body;
    determining on the basis of the calculated number of partial images, the size and position of said partial images, the partial image representing a part of the elongate body which is most susceptible to movement during said multiple shot irradiation covering a larger area than the area covered by partial images representing parts of the elongate body less susceptible to movement;
    pasting said partial images to form said image of said elongate body.

2. Method according to claim 1 wherein said image is a full spine image of a patient in up-right position and said partial image representing a part of the elongate body which is most susceptible to movement is the top partial image.

3. Method according to claim 1 wherein said image is a full leg image and said partial image representing a part of the elongate body which is most susceptible to movement is a partial image representing the bottom leg part.

4. Method according to claim 1 wherein the minimum number N of partial images required to image said elongate body is determined by the formula $$N = smallest\,integer \geq \left(\frac{L - \text{overlap}}{S - \text{overlap}}\right)$$

wherein L is the total length of the elongate body, overlap is a predefined amount of overlap and S is the size of the digital radiography detector.

5. An x-ray system for generating a radiation image of an elongate body by generating a sequence of partially overlapping partial radiation images of said elongate body by multiple shot irradiation and read out of a direct radiography detector, the x-ray system comprising:

an x-ray generation unit for generating x-rays;

an x-ray detection unit for detecting the x-rays after transmission through portions of the elongate body to generate partial images;

a controller that determines the total length of said elongate body to be imaged, calculates on the basis of said determined length overlap between said partial images and the number of partial images required to image said elongate body, determines on the basis of the calculated number of partial images, the size and position of said partial images, the partial image representing a part of the elongate body which is most susceptible to movement during said multiple shot irradiation covering a larger area than the area covered by partial images representing parts of the elongate body less susceptible to movement, and pastes said partial images to form said image of said elongate body.

* * * * *